United States Patent [19]
Sirotnak et al.

[11] Patent Number: 6,028,071
[45] Date of Patent: Feb. 22, 2000

[54] PURIFIED COMPOSITIONS OF 10-PROPARGYL-10-DEAZAAMINOPTERIN AND METHODS OF USING SAME IN THE TREATMENT OF TUMORS

[75] Inventors: Francis M. Sirotnak, New York, N.Y.; James R. Piper, Birmingham, Ala.; Joseph I. DeGraw, Missoula, Mont.; William T. Colwell, Menlo Park, Calif.

[73] Assignees: Sloan-Kettering Institute for Cancer Research, New York, N.Y.; SRI International, Menlo Park, Calif.; Southern Research Institute, Birmingham, Ala.

[21] Appl. No.: 09/214,984

[22] PCT Filed: Jul. 16, 1997

[86] PCT No.: PCT/US97/11982

§ 371 Date: Mar. 8, 1999

§ 102(e) Date: Mar. 8, 1999

[87] PCT Pub. No.: WO98/02163

PCT Pub. Date: Jan. 22, 1998

Related U.S. Application Data

[60] Provisional application No. 60/021,908, Jul. 17, 1996.

[51] Int. Cl.[7] .................. A61K 31/505; C07D 475/08
[52] U.S. Cl. .................. 514/249; 514/258; 544/260; 544/259
[58] Field of Search .................. 544/259, 260; 514/249, 258

[56] References Cited

U.S. PATENT DOCUMENTS 5,354,751  10/1994  DeGraw et al. .................. 514/249

OTHER PUBLICATIONS

Starling et al., Cancer Chemotherapy Report Part 1, vol. 58., No. 5., Sep./Oct. 1974.

J.I. DeGraw, W.T. Colwell, J.R. Piper, F.M. Sirotnak, "Synthesis and Antitumor Activity of 10–Propargyl–10–deazaaminopterin" *J. Med. Chem.*, 1993, vol. 36, pp. 2228–2231.

*Primary Examiner*—Mukund J. Shah
*Assistant Examiner*—Pavanaram K. Sripada
*Attorney, Agent, or Firm*—Oppedahl & Larson LLP

[57] ABSTRACT

Highly purified 10-propargyl-10-deazaaminopterin (10-propargyl-10dAM) compositions tested in xenograft models for their efficacy against human tumors are shown to be far superior to methotrexate ("MTX") and are even superior to the newer clinical candidate edatrexate ("EDX"). Moreover, 10-propragyl-10dAM showed a surprising ability to cure tumors such that there was no evidence of tumor growth several weeks after the cessation of therapy. Thus, highly purified compositions containing 10-propargyl-10dAM can be used to treat human tumors, particularly human mammary tumors and human lung cancer.

12 Claims, 5 Drawing Sheets

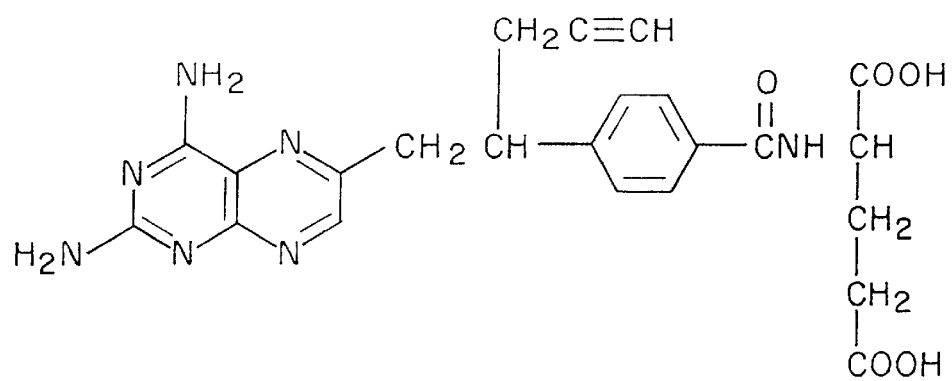
FIG. 1
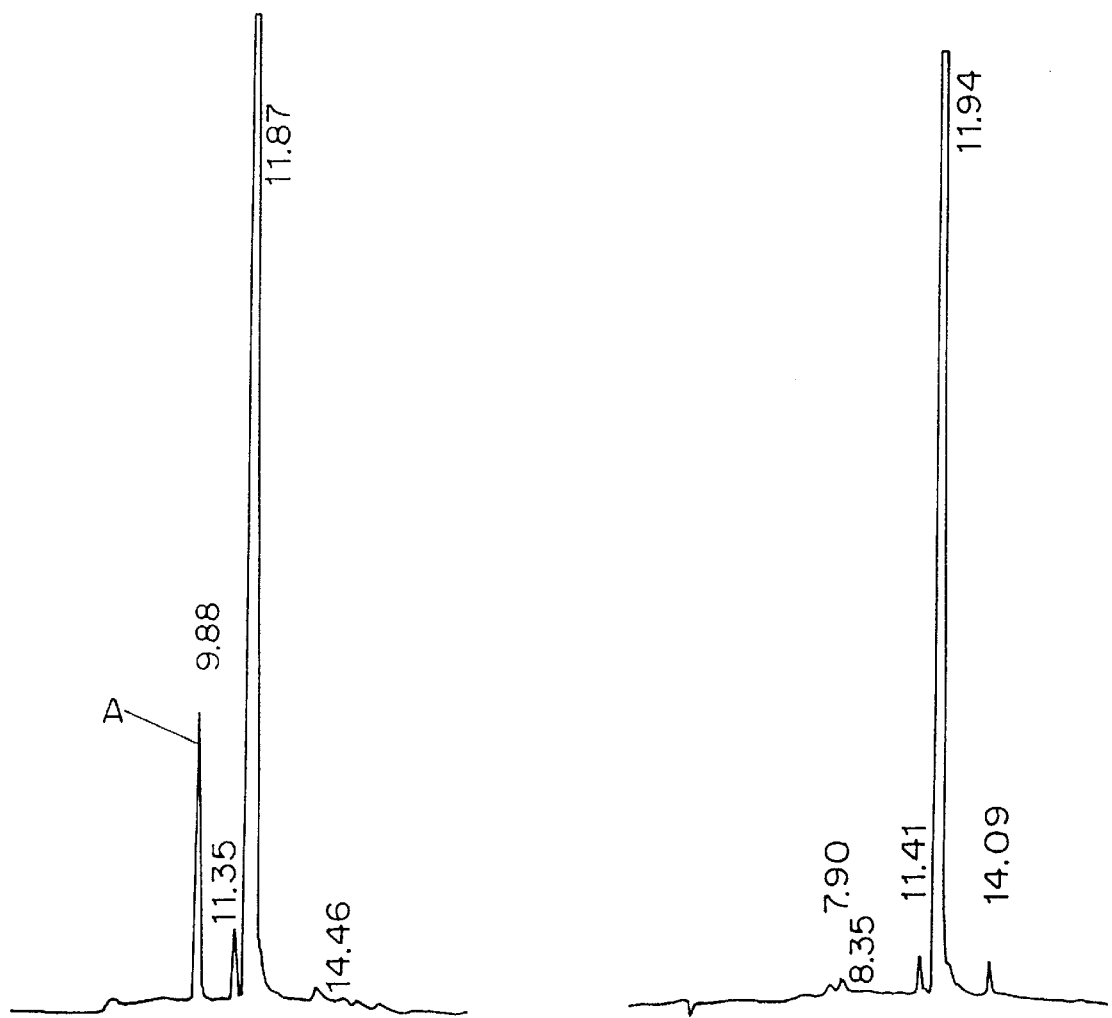
FIG. 2
FIG. 3 ns and is 371 of PCT/US97/11982 filed
PURIFIED COMPOSITIONS OF 10-PROPARGYL-10-DEAZAAMINOPTERIN AND METHODS OF USING SAME IN THE TREATMENT OF TUMORS This application is based on provisional appln 60/021,908 filed Jul. 17, 1996 and is 371 of PCT/US97/11982 filed Jul. 16, 1997.

BACKGROUND OF THE INVENTION

This application relates to a purified composition of the compound 10-propargyl-10-deazaaminopterin and to methods of using this compound in the treatment of tumors.

10-Propargyl-10-deazaaminopterin ("10-propargyl-10dAM") is a member of a large class of compounds which have been tested and in some cases found useful in the treatment of tumors. This compound, which has the structure shown in FIG. 1, was disclosed by DeGraw et al., "Synthesis and Antitumor Activity of 10-Propargyl-10-deazaaminopterin," J. Medical Chem. 36: 2228–2231 (1993) and shown to act as an inhibitor of growth in the murine L1210 cell line and to a lesser extent of the enzyme dihydrofolate reductase ("DHFR"). In addition, some results were presented for the antitumor properties of the compound using the E0771 murine mammary tumor model. This data was equivocal because of the small number of mice used in the test (3 per dosage), the absence of any standard deviation information which would quantify the reliability of the data, and the fact that the highest dose used was in fact toxic to the mice. Nevertheless, assuming this data has some predictive value for the efficacy of a drug in treating human tumors, it would at best predict a drug which, at equivalent levels of tolerance, had properties comparable to or perhaps slightly better than methotrexate.

SUMMARY OF THE INVENTION

Surprisingly, however, more highly purified 10-propargyl-10dAM compositions when tested in a xenograft model for their efficacy against human tumors have now been shown to be far superior to methotrexate ("MTX") and are even superior to edatrexate ("ETX"), a more recent clinical candidate. Moreover, 10-propargyl-10dAM showed a surprising ability to cure tumors such that there was no evidence of tumor growth several weeks after the cessation of therapy. Thus, a first aspect of the present invention is a highly purified composition containing 10-propargyl-10dAM. This composition can be used in accordance with the invention to treat tumors, particularly human mammary tumors and human lung cancer.

BRIEF DESCRIPTION OF THE DRAWINGS

FIG. 1 shows the structure of 10-propargyl-10dAM;

FIG. 2 shows an HPLC of an impure 10-propargyl-10dAM preparation prepared in accordance with the prior art;

FIG. 3 shows an HPLC of a highly purified 10-propargyl-10dAM preparation in accordance with the invention;

DETAILED DESCRIPTION OF THE INVENTION

Figure 4:
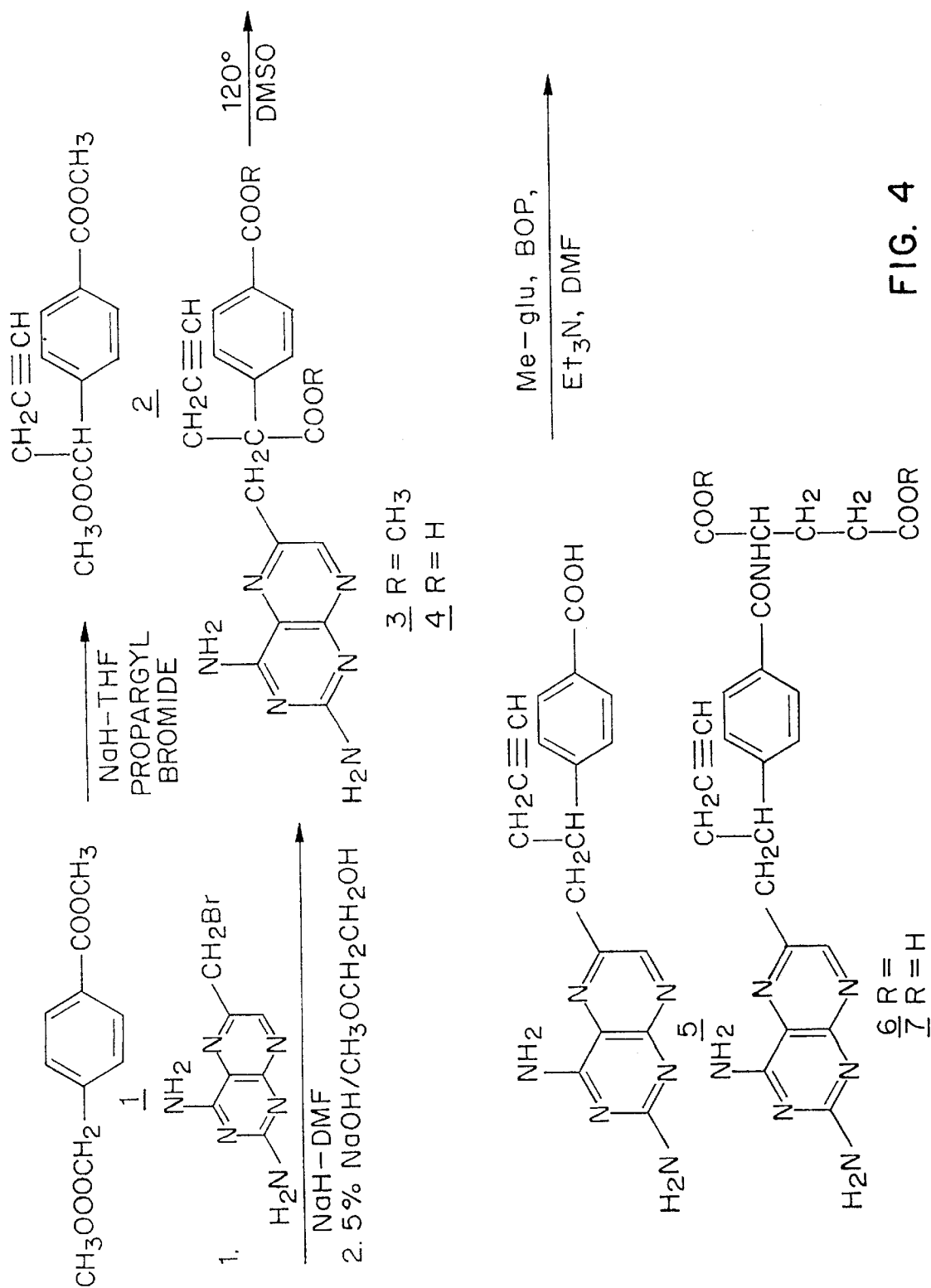
FIG. 4 shows a synthetic scheme useful in preparing the compound in accordance with the invention.

This application relates to "highly purified" 10-propargyl-10dAM. As used in the specification and claims hereof, compositions which are "highly purified" contain 10-propargyl-10dAM substantially free of other folic acid derivatives particularly 10-deazaaminopterin, which can interfere with the antitumor activity of the 10-propargyl-10dAM. A composition within the scope of the invention may include carriers or excipients for formulating the 10-propargyl-10dAM into a suitable dosage unit form for therapeutic use.

10-propargyl-10dAM can be synthesized using the method disclosed in the DeGraw paper, supra or in Example 7 of U.S. Pat. No. 5,354,751 which is incorporated herein by reference. HPLC evaluation of the product prepared by this method shows the presence of a substantial amount (~4.6%) of an impurity A (FIG. 2) which has a retention time consistent with 10-deazaaminopterin. Thus, if this synthetic approach is employed further purification is necessary beyond that disclosed in the DeGraw et al. paper. Such purification can be carried out by additional HPLC or crystallization to remove the 10-deazaaminopterin and other folic acid derivatives which may be present.

FIG. 3 shows an HPLC of a highly purified preparation consisting essentially of 10-propargyl-10dAM in accordance with the invention prepared using the method described in Example 1. In this case, the amount of 10-propargyl-10dAM (as determined by HPLC peak area) approaches 98%, and the peak corresponding to 10-deazaaminopterin is not detected by the processing software although there is a minor baseline ripple in this area.

The highly purified 10-propargyl-10dAM preparation in accordance with the invention was tested for cytotoxicity against human tumor cell lines and antitumor properties using xenografts of human tumor lines in nude mice as described in Example 2. The results of these tests are summarized in Tables 1 and 2. As shown, 10-propargyl-10dAM effected complete regressions of human MX-1 mammary carcinoma to a far greater extent than either MTX (which caused no regressions) or EDX, and was in fact able to effect cures in 9 out of the 20 mice tested. 10-propargyl-10dAM was also far more effective than MTX and EDX against xenografts of human LX-1 lung cancer and led to cures in 4 of the 10 mice tested. Similar results were observed for human A549 lung cancer cells. This level of efficacy is far in excess of anything which could have been predicted based upon the E0771 data which appeared in the DeGraw et al. paper. In fact, in that study no mice treated with the lower, non-toxic dosage level (24 mg/kg) of 10-propargyl-10dAM showed complete regression of the tumors and the average effect of the compound was no better than MTX. These 10-P-dAM treated mice showed an increase in tumor size at the end of three weeks, indicating that a cure had not been effected. It is therefore very surprising that the highly purified compound can be used against human tumors at much lower dosage levels (3 mg/kg) and achieve much higher levels of efficacy and many apparent cures.

While not intending to be bound by any particular mechanism for this increase in activity, it is believed that the presence of even relatively small amounts of other folic acid derivatives such as the 4.6% 10-deazaaminopterin observed in the samples prepared in the DeGraw et al paper can compete with the 10-propargyl-10dAM. effectively inhibiting its activity. This could happen at the level of polyglutamylation of 10-propargyl-10dAM by folyl polyglutamate synthetase in human tumor cells. The advantage of 10-propargyl-10dAM as substrate for this cytotoxic determinant could be compromised by the presence of 10-dAM which more effectively interacts with this enzyme, but it poorly metabolized thus competitively inhibiting the interaction of 10-propargyl-10dAM with that enzyme. Regardless of the mechanism, however, the highly purified compositions of the invention are markedly more active against human cancer cells than would be predicted based upon the data presented in the DeGraw paper. This is also shown by the increased cytotoxicity of 10-propargyl-10dAM compared to EDX against human tumor cells that was consistently found, and which contrasts with the relative equivalence of these two compounds against murine tumor cells lines as reported by DeGraw et al. This enhanced activity against human tumor cells can be used to provide therapeutic benefits to human patients suffering from cancer, particularly from breast cancer or lung cancer.

For this purpose, the highly purified 10-propargyl-10dAM is advantageously formulated as part of a pharmaceutical preparation. The specific dosage form will depend on the method of administration, but may include tablets, capsules, oral liquids, and injectable solutions for intravenous, intramuscular or intraperitoneal administration. Based upon the relative effectiveness of MTX, EDX and 10-Propargyl-10-deazaaminopterin, substantially free of 10-deazaaminopterin against human xenograft tumors, and on the dosages of MTX and EDX found to be appropriate in human clinical trials, dosages of 10-Propargyl-10-deazaaminopterin, substantially free of 10-deazaaminopterin in the range of from 40 to 120 mg/m$^2$ of body surface area/day should be effective, depending on the treatment schedule. Higher doses would appear to be contraindicated because of the toxicity observed at such levels in animal studies reported below.

10-Propargyl-10-dAM in accordance with the invention may also be formulated in combination with a variety of other cytotoxic and antitumor compounds, including vinca alkaloids such as vinblastine, navelbine and vindesine; 5-fluorouracil; alkylating agents such as cyclophosphamide or ifosfamide: cisplatin or carboplatin; leucovorin; taxols such a paclitaxel or docetaxel; and antibiotics such as doxorubicin and mitomycin. Combinations of 10-propargyl-10dAM with several of these other antitumor agents may also be used.

EXAMPLE 1

FIG. 4 shows a synthetic scheme useful in preparing 10-propargyl-10-dAM in accordance with the invention. A mixture of 60% NaH in oil dispersion (1.06 g, 26.5 mmol) in 18 mL of sieve-dried THF was cooled to 0° C. The cold mixture was treated with a solution of homoterephthalic acid dimethyl ester (5.0 g, 24 mmol. compound 1 in FIG. 4) in dry THF (7 mL), and the mixture was stirred for 1 hour at 0° C. Propargyl bromide (26.4 mmol) was added, and the mixture was stirred at 0° C. for an additional 1 hour, and then at room temperature for 16 hours. The resulting mixture was treated with 2.4 mL of 50% acetic acid and then poured into 240 mL of water. The mixture was extracted with ether (2×150 mL). The ether extracts were combined, dried over Na$_2$SO$_4$, and concentrated to an orange-yellow oil. Chromatography on silica gel (600 mL of 230–400 mesh) with elution by cyclohexane-EtOAc (8:1) gave the product α-propargylhomoterephthalic acid dimethyl ester (compound 2) as a white solid (4.66) which appeared by TLC (cyclohexane-EtOAc, 3:1) to be homogeneous. Mass spectral data on this product, however, showed it to be a mixture of the desired product 2, and the dipropargylated compound. No starting material 1 was detected. HPLC shows the ratio of mono- to di-propargylated products to be about 3:1. Since the dipropargylated product, unlike compound 1, cannot produce an unwanted coproduct in the next step of the reaction, this material was suitable for conversion to compound 3. Absence of starting compound 1 in the product used to proceed in the synthesis is very important in order to avoid the sequential formation of 10-dAM during the transformations lading to the final product, because complete removal from 10-dAM from 10-propargyl-1-dAM is very difficult.

A mixture was formed by combining 0.36 g of a 60% NaH (9 mmol) in oil dispersion with 10 mL of dry DMF and cooled to 0–5° C. The cold mixture was treated drop-wise with a solution of the product of the first reaction (compound 2) (2.94 g, 12 mmol) in 10 mL dry DMF and then stirred at 0° C. for 30 minutes. After cooling to –25° C., a solution of 2,4,diamino-6-(bromomethyl)pteridine hydrobromide-0.2 2-propanol (1.00 g, 2.9 mmol) in 10 mL dry DMF was added drop-wise while the temperature was maintained near –25° C. The temperature of the stirred mixture was allowed to rise to –10° C. over a period of 2 hours. After an additional 2 hours at –10° C., the temperature was allowed to rise to 20° C., stirring at room temperature was continued for 2 hours longer. The reaction was then adjusted to pH 7 by addition of solid CO$_2$, After concentration in vacuo to remove solvent, the residue was stirred with diethyl ether and the ether insoluble material was collected, washed with water, and dried in vacuo to give 1.49 g of a crude product. This crude product was dissolved in CHCl$_3$—MeOH (10:1) for application to a silica gel column. Elution by the same solvent system afforded 10-propargyl-10-carbomethoxy-4-deoxy-4-amino-10-deazapteroic acid methyl ester (compound 3) which was homogenous to TLC in 40% yield (485 mg).

A stirred suspension of compound 3 (400 mg, 0.95 mmol) in 2-methoxyethanol (5 mL) was treated with water (5 mL) and then 10% sodium hydroxide solution (3.9 mL). The mixture was stirred as room temperature for 4 hours, during which time solution occurred. The solution was adjusted to pH 8 with acetic acid and concentrated under high vacuum. The resulting residue was dissolved in 15 mL of water and acidified to pH 5.5–5.8 resulting in formation of a precipitate. The precipitate was collected, washed with water and dried in vacuo to recover 340 mg of compound 4 (91% yield). HPLC analysis indicated a product purity of 90%.

Compound 4 (330 mg) was decarboxylated by heating in 15 mL DMSO at 115–120° C. for 10 minutes. A test by HPLC after 10 minutes confirmed that the conversion was essentially complete. DMSO was removed by distillation in vacuo (bath at 40° C.). The residue was stirred with 0.5 N NaOH to give a clear solution, Acidification to pH 5.0 with 1 N HCl gave 10-propargyl-4-deoxy-4-amino-10-deazapteroic acid (compound 5) as a yellow solid in 70% yield. HPLC indicated product purity at this stage as 90%.

Compound 5 (225 mg, 0.65 mmol) was coupled with dimethyl L-glutamate hydrochloride (137 mg, 0.65 mmol) using BOP reagent (benzotriazole-1-yloxytris (dimethylamino) phosphonium hexafluorophosphate (287 mg, 0.65 mmol, Aldrich Chemical Co.) in DMF (10 mL) containing triethylamine (148 mg, 1.46 mmol). The mixture was stirred for 3 hours at 20–25° C. and then evaporated to dryness. The residue was stirred with water, and the water-insoluble crude product was collected and dried in vacuo. The crude product (350 mg) was purified by silica gel chromatography with elution by CHCl₃—MeOH (10:1) containing triethylamine (0.25% by volume) to recover 165 mg of 10-propargyl-10-deazaaminopterin dimethyl ester (compound 6, 50% yield) which was homogeneous to TLC (CHCl₃—MeOH 5:1).

Compound 6 (165 mg, 0.326 mmol) was suspended in 10 mL stirred MeOH to which 0.72 mL (0.72 meq) 1 N NaOH was added. Stirring at room temperature was continued until solution occurred after a few hours. The solution was kept at 20–25° C. for 8 hours, then diluted with 10 mL water. Evaporation under reduced pressure removed the methanol, and the concentrated aqueous solution was left at 20–25° C. for another 24 hours. HPLC then showed the ester hydrolysis to be complete. The clear aqueous solution was acidified with acetic acid to pH 4.0 to precipitate 10-propargyl-10-deazaaminopterin as a pale yellow solid, The collected, water washed and dried in vacuo product weighed 122 mg (79% yield). Assay by elemental analysis, proton NMR and mass spectroscopy were entirely consistent with the assigned structure. HPLC analysis indicated purity of 98% and established the product to be free of 10-deazaaminopterin.

EXAMPLE 2

The highly purified 10-propargyl-10dAM preparation prepared in accordance with Example 1 was tested for antitumor properties using xenografts of human tumor lines in nude mice. Xenografts of human MX-1 mammary carcinoma were implanted into nude mice by standard procedures.

To test the antitumor properties of 10-propargyl-10dAM against these tumor cells, 3 mg/kg of the compound was administered once a day to each of twenty mice for a total of five days starting three days after tumor implantation. For comparison, untreated controls (20 mice), methotrexate treated mice (10 mice; dosage 2 mg/kg on the same treatment schedule) and edatrexate treated mice (20 mice; dosage 1.5 mg/kg on the same treatment schedule) were also evaluated. These doses are all "maximum tolerated doses" and thus are an appropriate basis for comparison based upon equitoxicity. Average tumor diameter was measured 14 days after the start of treatment, i.e., 7 days after the cessation of treatment. Mice which had no measurable tumor at this time were considered to have undergone a complete regression. In addition, mice which were tumor free at 14 days were checked three weeks after cessation of therapy for the reappearance of tumors. Tumor free mice at the end of three weeks after therapy were considered to be cured. The results are summarized in Table 1.

TABLE 1

| Treatment | Average Tumor Diameter (mm) | Complete Regressions | Cures |
| --- | --- | --- | --- |
| untreated | 8.6 ± 0.9 | 0/20 | 0/20 |
| MTX | 7.6 ± 0.8 | 0/10 | 0/10 |
| EDX | 2.2 ± 1.1 | 6/20 | 2/20 |
| 10-propargyl-10 dAM | 0.3 | 13/20 | 9/20 |

As can be seen, 10-propargyl-10dAM is substantially more effective than either MTX or EDX, and effected a substantial number of cures.

EXAMPLE 3

Example 2 was repeated using xenografts of human LX-1 lung cancer in nude mice. The results are summarized in Table 2.

TABLE 2

| Treatment | Average Tumor Diameter (mm) | Complete Regressions | Cures |
| --- | --- | --- | --- |
| untreated | 10.2 ± 1.8 | 0/10 | 0/10 |
| MTX | 9.2 ± 2 | 0/10 | 0/10 |
| EDX | 4.3 ± 2 | 3/10 | 1/10 |
| 10-propargyl-10 dAM | 0.4 | 9/10 | 4/10 |

Again, 10-propargyl-10dAM was shown to be substantially more effective than MTX or EDX, and effected a substantial number of cures.

EXAMPLE 4

Example 2 was repeated using xenografts of human A549 lung cancer in nude mice. The results are summarized in Table 3.

TABLE 3

| Treatment | Average Tumor Diameter (mm) | Complete Regressions | Cures |
| --- | --- | --- | --- |
| untreated | 8.9 ± 1 | 0/5 | 0/5 |
| MTX | 8.3 ± 2 | 0/5 | 0/5 |
| EDX | 6.8 ± 2 | 0/5 | 0/5 |
| 10-propargyl-10 dAM | 4.2 ± 2 | 3/10 | 2/10 |

Again, 10-propargyl-10dAM was shown to be substantially more effective than MTX or EDX, and effected a substantial number of cures.

EXAMPLE 5

Cytotoxicity studies were performed on four human tumor cells lines to compare the cytotoxicity of EDX to 10-propargyl-10dAM using a 3 hour pulse-exposure to each compound. Three replicate experiments of each cell line were tested for each compound. The results are summarized in Table 4.

TABLE 4

| Tumor | Tissue Type | $IC_{50}$ - EDX | $IC_{50}$ 10-propargyl-10 dAM |
| --- | --- | --- | --- |
| MDA468 | lung | 0.38 ± 0.05 | 0.11 ± 0.01 |
| SKLC-16 | lung | 0.26 ± 0.03 | 0.10 ± 0.014 |
| ZR-75-1 | mammary | 0.86 ± 0.1 | 0.28 ± 0.05 |
| SK-BRIII | mammary | 0.99 ± 0.15 | 0.14 ± 0.02 |

In each case, the 10-propargyl-10dAM was substantially more cytotoxic than EDX against the human tumor cells lines.

EXAMPLE 6

Toxicity of 10-propargyl-10dAM was assessed in rats, mice and dogs. Male CD rats and male B6D2F₁ mice (Charles River Breeding Laboratories, Wilmington, Mass.) and young adult male beagle dogs (Marshall Frams USA. Inc., Northrose, N.Y.) were used in the tests. All animals were maintained in environmentally controlled rooms with a 12 hours light/12 hour dark light cycle. Mice and rats were received when 5 weeks old and were observed for 1 to 2 weeks before study and used only if their growth during the preliminary observation matched laboratory standards for weight-gain. Dogs were observed at least 2–3 weeks before use, during which period they were weighted and examined at regular intervals to assure good health. During the test period, all animals were weighted daily and observed for appetite, stool conditions, general appearance and signs of toxicity. Dogs were also examined daily to monitor body temperature, heart rate, and respiration rate.

For all treatments, the dose of drug was weighed and dissolved in isotonic bacteriostatic saline by addition of about 2 molar equivalents of 1 N NaOH. The pH of this solution was adjusted to 7–7.2 by addition of NaOH solution as determined using a pH meter. Solutions were used either immediately or after thawing preparations that had been stored at −20° C. Injections in mice and rats were made in a constant volume of 0.01 ml/g of body weight.

Toxicity in Mice

B6D2F$_1$ mice, five per group, were given 10-propargyl-10dAM i.p. weekly for three weeks (days 1, 8 and 15) at varying concentrations as summarized in Table 5.

TABLE 5

| Treatment Level | Survivors After 32 days |
| --- | --- |
| control | 5/5 |
| 100 mg/kg | 5/5 |
| 200 mg/kg | 5/5 |
| 300 mg/kg | 5/5 |
| 400 mg/kg | 1/5 |
| 600 mg/kg | 1/5 |

Figure 5:
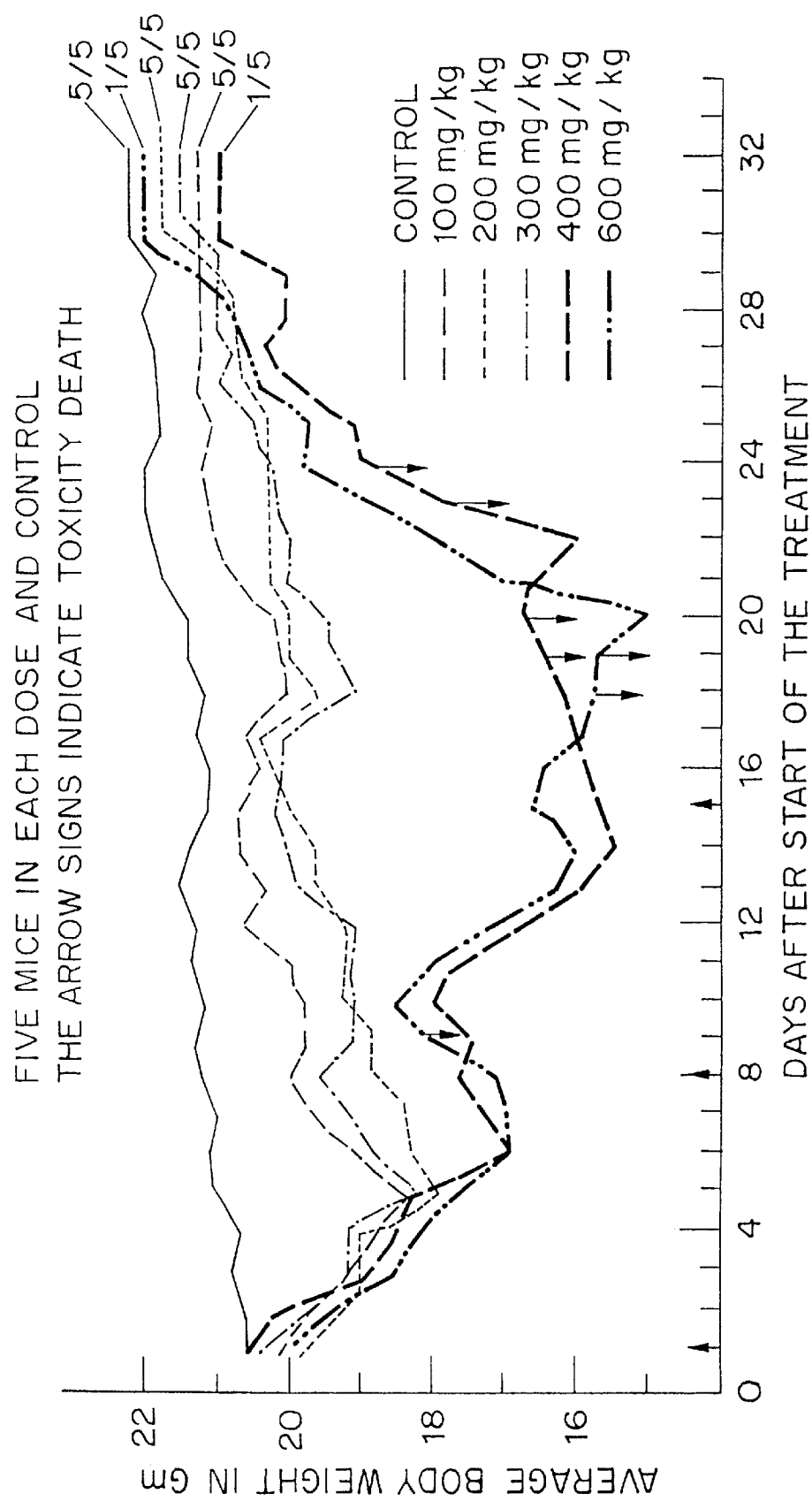
FIG. 5 summarizes the results of toxicity testing in mice.

The results of body weight changes and lethality are summarized in FIG. 5. As shown, at 100, 200 and 300 mg/kg there were initial moderate declines in body weight (up to 2 grams), but no further drops in the subsequent doses. All mice in these three dosage groups regained weight in weeks 3 and 4 and survived. At dosages of 400 mg/kg, i.p. QWX3, four out of five mice died on days 19, 20, 23 and 24, and a 600 mg/kg, four out of five mice died on days 9, 18, 19 and 21. Those animals treated with the higher two doses had more than 20% weight loss, ruffled fur and diarrhea. However, surviving mice gained weight and caught up with the control group two weeks after the final injections. The approximate LD_was about 370 mg/kg. i.p. QWX3 when estimated with dose effect relationship and the median-effect plot. (Chou et al, *Encyclopedia of Human Biology*, R. Dalbecco, ed., Vol. 2, pp. 271–279, Academic Press, 1991.)

Toxicity in Rats

CD rats, five per group, were given 10-propargyl-10dAM i.v. weekly for three weeks (days 1, 8 and 15) at varying concentrations as summarized in Table 6.

TABLE 5

| Treatment Level | Survivors After 32 days |
| --- | --- |
| control | 5/5 |
| 50 mg/kg | 5/5 |
| 100 mg/kg | 4/5 |
| 150 mg/kg | 2/5 |
| 200 mg/kg | 0/5 |
| 300 mg/kg | 0/5 |

Figure 6:
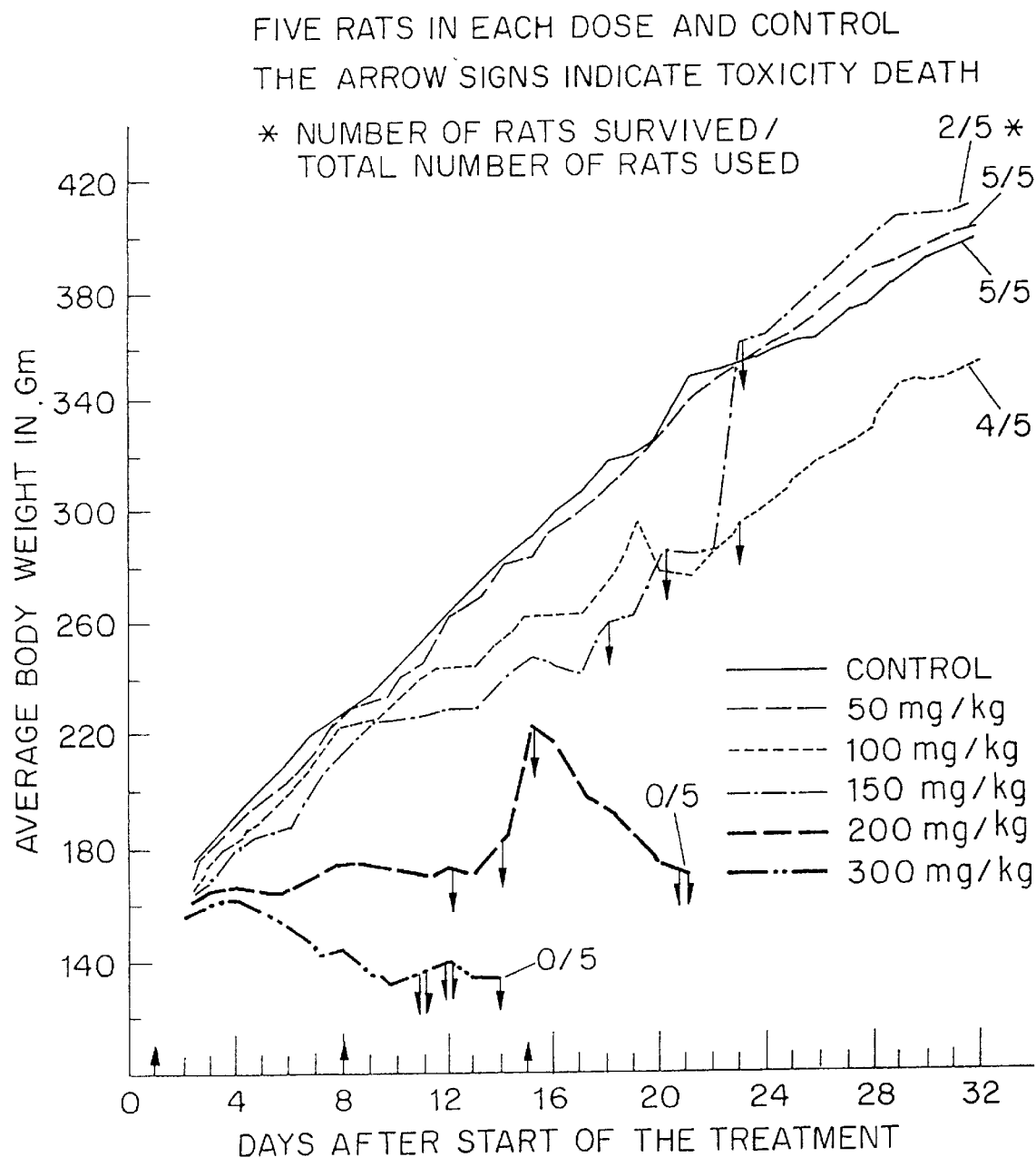
FIG. 6 summarizes the results of toxicity testing in rats.

The results of body weight changes and lethality are summarized in FIG. 6. At 50 mg/kg, i.v. QWX3, no apparent changes in body weight were observed; at 100 mg/kg, there were approximately 10 gram decreases in body weight at the third dose, and one out of the five animals had died by day 23. The remaining animals gained weight, but at a rate less than that of control animals.

At 150 mg/kg, i.v. QWX3, three out of the five rats died on days 18, 20, and 23. At 200 mg/kg, i.v. QWX3 all five rats died on days 12, 14, 15, 20 and 20, respectively. At 300 mg/kg, i.v. QWX3 all five rats also died, but somewhat sooner that those on the 200 mg/kg dosage, on days 11, 11, 12, 12, and 14, respectively. No immediate toxicity was observed in any of the rats immediately after injection at the 150–300 mg/kg dosages. These rats began to lose weight the following day, and had ruffled fur with evidence of diarrhea and dehydration which culminated one to three days before death. These signs persisted through the course of the experiment and were exacerbated by the second and third injections.

The data from these experiments did not allow a precise calculation of $LD_{10}$ or $LD_{50}$. A conservative estimate of $LD_{10}$ in rats with the dose-effect relationship and the median-effect plot is about 75 mg/kg, i.v. QWX3 and $LD_{50}$ is about 110 mg/kg i.v. QWX3.

Toxicity in Dogs

Eight male beagles weighing 9.4 to 10.6 pounds were divided into four pairs. The pairs were treated with intravenous injections of 10-propargyl-10dAM weekly for three weeks (days 1, 8 and 15) at 0 mg/kg (dogs A and B); 3 mg/kg (dogs C and D); 8 mg/kg (dogs E and F) and 12 mg/kg (dogs G and H). At 3 mg/kg and 8 mg/kg, a maximal body weight decrease of 2 to 3 kg occurred on day 20. followed by body weight recovery thereafter through the end of the 35 day observation period. At 12 mg/kg there were steady declines in body weight totaling up to 3 kg (or more than 20% loss), and the animals became moribund on day 12 and 14, prior to the third dosage.

Major signs of toxicity were observed for the dogs treated at 8 mg/kg or 12 mg/kg, including vomiting, diarrhea, watery or bloody stool, lethargy, anoreptic, and generalized weakness. At 3 mg/kg, i.v. QWX3, no symptoms were apparent. The estimated $LD_{50}$ is about 8 mg/kg, i.v., QWX3.

Blood samples were drawn from each of the dogs during the testing. No marked or persistent change sin blood chemistry or blood cell counts were observed, except at terminal phases of toxicity. There were some declines in white blood cells, lymphocytes, neutrophil counts, decreases in hemoglobin, total protein and albumin, and increases in amylase and monocytes were observed, especially at the higher two doses.

Dogs G and H were euthanized and a complete necropsy was performed on days 12 and 14, respectively. One animal from each of the other pairs were euthanized for histopathological examination on day 33 (dog E) or 34 (dogs B and C) of the experiment.

In Dog G, most of the organs appeared normal. The mucosa of small and large intestines showed edema and hemorrhagic. Stomach and the large and small intestines were empty. Dog H was severely depressed, with shallow breathing and reduced heart rate on day 14 prior to euthanasia. Upon euthanasia, the stomach was found to be filled with bile-tinged mucous, and the intestines were filled with watery stool but no signs of blood. No ulcers in the stomach, intestine or esophagus were observed. The liver was pale and spotty. The spleen was dark purple and rough on the surface.

For dog E which received 8 mg/kg, i.v. QWX3, most organs appeared normal but both sides of the lung were pink with a few bloody spots. Large and small intestines and liver showed lavender color and kidneys showed edema and purple color. Stomach and intestines were full with food, and bladder full with urine.

Dog C, which received 3 mg/kg, i.v. QWX3, appeared normal on day 34 prior to euthanasia. Most organs appeared normal. The right lung was pink, large and small intestines purple in color. Liver showed dark purple color. Stomach and intestines were full with food, and bladder full with urine.

Histopathological examination of tissues of dogs treated with 0 mg/kg and 3 mg/kg i.v., QWX3, showed no significant lesions in the organ specimens collected. At 8 mg/kg, i.v. QWX3, the large intestines and multicocal mild colitis. At 12 mg/kg, i.v. QWX3, subacute to chronic ulcerative esophagitis and severe necrotizing enterocolitis were observed. Other organs, e.g., brain, heart, liver, lung, kidney, salivary gland, testis and spleen showed no significant lesions.

EXAMPLE 7

To monitor the pharmacokinetics of the 10-propargyl-10dAM, single doses of 3 mg/kg were given intravenously to each of two dogs, I and J. Blood samples were collected at −5 min, 5 min, 10 min, 20 min, 30 min, 45 min, 60 min, 90 min, 3 hr, 4 hr, 6 hr, 24 hr, 30 hr and 48 hr. 10-propargyl-10dAM concentrations in plasma were determined by a fluorometric high performance liquid chromatography (HPLC) method using an Econosphere C18 column, 15% acetonitrile/$KH_2PO_4$ 50 mm mobile phase, pH 7.0, with a 1 ml/min flow rate at room temperature. The injection volume was 1 ul. The retention time of 10-propargyl-10dAM was 18.5 minutes.

Figure 7:
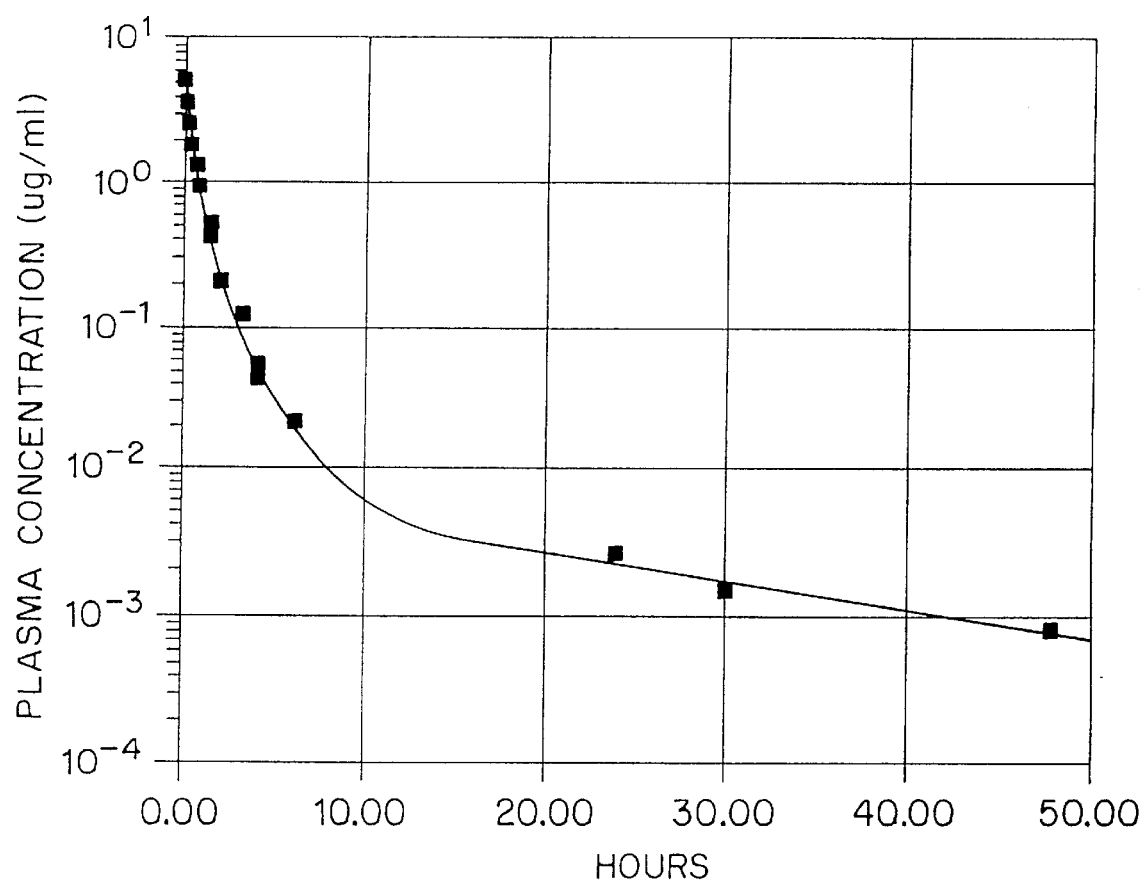
FIG. 7 shows average plasma concentrations after administration of 10-propargyl-10dAM in dogs.

The plasma half-life ($t_{1/2}$) for dog I were 26.7 min. 0.49 hrs and 37.4 hours for α, β and γ phases of the kinetics. For dog J, the observed $t_{1/2}$ values were 21.2 min, 1.26 hrs and 16.3 hrs. The average plasma concentrations at various times are shown in FIG. 7.

Urine specimens were collected from each dog at 30 min, 1 hr, 2 hr and 4 hr following administration of 10-propargyl-10dAM and analyzed by HPLC. 10-propargyl-10dAM was mainly excreted unchanged (retention time 18.5 minutes). There were small amounts of a metabolite with a retention time of 6.3 min which account for <0.31% and <3.5% of the total urinary 10-propargyl-10dAM at 1 hr and 4 hr, respectively.

What is claimed is:

1. 10-Propargyl-10-deazaaminopterin, substantially free of 10-deazaaminopterin.

2. A composition consisting essentially of 10-Propargyl-10-deazaaminopterin.

3. A pharmaceutical composition comprising 10-Propargyl-10-deazaaminopterin, substantially free of 10-deazaaminopterin, and a pharmaceutically acceptable carrier.

4. A method for treatment of tumors comprising administering to a human patient diagnosed as having a tumor a therapeutically effective amount of 10-propargyl-10-deazaaminopterin, substantially free of 10-deazaaminopterin.

5. The method according to claim 4, wherein the tumor is a solid tumor.

6. The method according to claim 4, wherein the 10-propargyl-10-deazaaminopterin, substantially free of 10-deazaaminopterin, is administered in amounts of from 40 to 120 $mg/m^2$ of body surface area/day.

7. The method according to claim 5, wherein the tumor is a mammary tumor.

8. The method according to claim 4, wherein the tumor is a lung tumor.

9. The pharmaceutical composition according to claim 3, further comprising at least one additional cytotoxic or antitumor compound.

10. The pharmaceutical composition according to claim 9, wherein the at least one additional cytotoxic or antitumor compound is selected from the group consisting of vinca alkaloids, 5-fluorouracil, alkylating agents, cisplatin, carboplatin, leucovorin, taxols and antibiotics.

11. The method according to claim 4, wherein at least one additional cytotoxic or antitumor compound is administered with the therapeutically effective amount of 10-propargyl-1-deazaaminopterin, substantially free of 10-deazaaminopterin.

12. The method according to claim 11, wherein the at least one additional cytotoxic or antitumor compound is selected from the group consisting of vinca alkaloids, 5-fluorouracil, alkylating agents, cisplatin, carboplatin, leucovorin, taxols and antibiotics.

* * * * *

UNITED STATES PATENT AND TRADEMARK OFFICE
CERTIFICATE OF CORRECTION

| | |
|---|---|
| PATENT NO. | : 6,028,071 |
| APPLICATION NO. | : 09/214984 |
| DATED | : February 22, 2000 |
| INVENTOR(S) | : Sirotnak et al. |

Page 1 of 1

It is certified that error appears in the above-identified patent and that said Letters Patent is hereby corrected as shown below:

Column 1, Line 9 please insert: This application was supported by NIH grant number CA56517. The US government has certain rights in this invention.

Signed and Sealed this

Eighth Day of April, 2008

JON W. DUDAS
*Director of the United States Patent and Trademark Office*